(12) United States Patent
Bruijns

(10) Patent No.: US 12,016,928 B2
(45) Date of Patent: Jun. 25, 2024

(54) COMPOSITION AS AUXILIARY MEANS FOR ORAL MEDICATION

(71) Applicant: PAXTREE LTD., Nicosia (CY)

(72) Inventor: Ron Bruijns, Raamsdonkveer (NL)

(73) Assignee: PAXTREE LTD., Nicosia (CY)

( * ) Notice: Subject to any disclaimer, the term of this patent is extended or adjusted under 35 U.S.C. 154(b) by 0 days.

(21) Appl. No.: 17/864,332

(22) Filed: Jul. 13, 2022

(65) Prior Publication Data

US 2022/0347303 A1    Nov. 3, 2022

Related U.S. Application Data

(62) Division of application No. 17/028,829, filed on Sep. 22, 2020, now Pat. No. 11,419,940, which is a division of application No. 16/243,857, filed on Jan. 9, 2019, now Pat. No. 10,814,005, which is a division of application No. 14/782,008, filed as application No. PCT/NL2014/050199 on Apr. 2, 2014, now abandoned.

(30) Foreign Application Priority Data

Apr. 2, 2013 (NL) ...................................... 2010552

(51) Int. Cl.
| | |
|---|---|
| A61K 47/36 | (2006.01) |
| A23L 29/256 | (2016.01) |
| A23L 29/30 | (2016.01) |
| A61K 9/00 | (2006.01) |
| A61K 9/06 | (2006.01) |
| A61K 31/194 | (2006.01) |
| A61K 47/02 | (2006.01) |
| A61K 47/12 | (2006.01) |
| A61K 47/26 | (2006.01) |

(52) U.S. Cl.
CPC ............ *A61K 47/36* (2013.01); *A23L 29/256* (2016.08); *A23L 29/35* (2016.08); *A61K 9/0053* (2013.01); *A61K 9/0056* (2013.01); *A61K 9/06* (2013.01); *A61K 31/194* (2013.01); *A61K 47/02* (2013.01); *A61K 47/12* (2013.01); *A61K 47/26* (2013.01)

(58) Field of Classification Search
CPC ...... A61K 47/36; A61K 9/0056; A23L 29/256
See application file for complete search history.

(56) References Cited

U.S. PATENT DOCUMENTS

| | | | | |
|---|---|---|---|---|
| 5,002,934 A | * | 3/1991 | Norton .................. | A23L 29/256 514/846 |
| 2003/0108607 A1 | * | 6/2003 | Szymczak ............. | A61K 9/286 424/479 |
| 2006/0068074 A1 | * | 3/2006 | Stefandl ................ | A23L 29/256 426/573 |
| 2007/0128285 A1 | | 6/2007 | Jin et al. | |
| 2009/0155363 A1 | * | 6/2009 | Maibach ............... | A61K 9/0056 514/777 |
| 2012/0022104 A1 | | 1/2012 | Takanashi | |

FOREIGN PATENT DOCUMENTS

| | | | | |
|---|---|---|---|---|
| FR | 1039241 | | 6/2012 | |
| JP | 2003-104912 | | 4/2003 | |
| NL | 1 039 241 | | 6/2012 | |
| WO | 0056176 | | 9/2000 | |
| WO | WO-0056176 A1 | * | 9/2000 | ........... A23C 9/1542 |
| WO | 2004/091528 | | 10/2004 | |

OTHER PUBLICATIONS

Thrimawithana, T.R. et al. "Texture and rheological characterization of kappa and iota carrageenan in the presence of counter ions" Carbohydrate Polymers 82 (2010) 69-77 (Year: 2010).*
Udomrati et al. "Rheological properties and stability of oil-in-water emulsions containing tapioca maltodextrin in the aqueous phase" Journal of Food Engineering 116 (2013) 170-175 (Year: 2013).*
International Search Report for PCT/NL2014/050199 mailed May 16, 2014, 3 pages.
Written Opinion of the ISA for PCT/NL2014/050199 mailed May 16, 2014, 7 pages.
International Preliminary Report on Patentability for PCT/NL2014/050199 mailed Jun. 25, 2015, 15 pages.
Thrimawithana, T.R. et al; "Texture and rheological characterization of kappa and iota carrageenan in the presence of counter ions" Carbohydrate Polymers 82 (2010) 69-77.
Rowe, R.C. et al, Handbook of Pharmaceutical Excipients, sixth edition. Pharmaceutical Press 2009, pp. 1-888 (Year: 2009).

* cited by examiner

*Primary Examiner* — Andrew S Rosenthal
(74) *Attorney, Agent, or Firm* — NIXON & VANDERHYE P.C.

(57) ABSTRACT

Compositions, specifically a jelly, are provided the use of which composition as an auxiliary means eases the taking of oral medication in solid form, which composition comprises iota-carrageenan as a jellifying agent and citric acid as a salivating agent, characterized in that the composition further comprises maltodextrin. In another aspect, the composition comprises a calcium sequestrant for adjusting Ca-ion activity of the composition. In one embodiment, the composition comprises iota-carrageenan in 0.7-1.0% in mass, citric acid in 0.06-0.07% in mass, maltodextrin in 1.5% in mass, all relative to the total mass of the composition, and an amount of a calcium sequestrant such that the Ca-ion activity of the composition is between 20 ppm and 80 ppm.

27 Claims, 9 Drawing Sheets

COMPOSITION AS AUXILIARY MEANS FOR ORAL MEDICATION

CROSS-REFERENCE TO RELATED APPLICATIONS

This application is a divisional of U.S. application Ser. No. 17/028,829 (now U.S. Pat. No. 11,419,940), which in turn is a divisional of U.S. application Ser. No. 16/243,857 (now U.S. Pat. No. 10,814,005), which is a divisional of U.S. application Ser. No. 14/782,008 filed on Apr. 2, 2014 (now abandoned), which is the U.S. national phase of International Application No. PCT/NL2014/050199 filed 2 Apr. 2014, which designated the U.S. and claims priority to NL Patent Application No. 2010552 filed 2 Apr. 2013, the entire contents of each of which are hereby incorporated by reference.

FIELD OF THE INVENTION

The present invention relates to the technical field of taking oral medication. The present invention relates to a composition, specifically a jelly, the use of which is to ease the taking of oral medication in solid form, and to the use of such a composition as an auxiliary means for the stated purpose.

BACKGROUND OF THE INVENTION

Some people, inter alia young children and elderly people, experience swallowing problems when taking oral medication. This problem may be caused by certain conditions such as dysphagia and/or xerostomia (hypo salivation, dry mouth), and it can also have a psycho-somatic cause, e.g. a physiological abnormality, or disgust regarding the size or taste of the capsules or pills to be swallowed.

Several compositions according to the pre-amble are known from the prior art. The following relate to the use of a jelly or jelly-like composition to enhance swallowing and ingestion of solid medication. One known composition that facilitates swallowing comprises a mixture of modified pre-gelatinized starch, a sugar alcohol and a water-soluble food fiber. Another known composition comprises a combination of two polysaccharides and a xanthan gum and/or a carrageenan to improve the function of ingestion/swallowing. Yet another known composition comprises a coating for a medication, the coating comprising a lubricating jelly that comprises gelatin and hydroxypropyl methylcellulose. Yet another known composition comprises iota-carrageenan as a jellifying agent and citric acid as a salivating agent.

All presently known compositions, specifically jellies, the use of which is to ease the taking of oral medication in solid form, and to the use of such compositions as auxiliary means for the stated purpose, have their own disadvantages. One known composition is limited to mixing it with medication in powder form only. The use of another known composition provides an unstable suspension upon mixing with the intended medication. Yet another known composition has to be prepared each and every time for every active standard and every dosage of the active substance of the medication.

An object of the present invention is to provide an alternative composition, specifically a jelly, the use of which composition is as an auxiliary means to ease the taking of oral medication in solid form, which composition comprises iota-carrageenan as a jellifying agent and citric acid as a salivating agent.

It is another object of the present invention to provide an alternative composition, specifically a jelly, the use of which composition is as an auxiliary means to ease the taking of oral medication in solid form, which composition comprises iota-carrageenan as a jellifying agent and citric acid as a salivating agent, which composition can be mixed with oral medication in all known solid forms including pills, capsules, tablets and powders.

It is a further object of the invention to provide an alternative composition, specifically a jelly, the use of which composition as an auxiliary means is to ease the taking of oral medication in solid form, which composition comprises iota-carrageenan as a jellifying agent and citric acid as a salivating agent, which composition upon mixing with oral medication can provide a stable suspension that can be swallowed or ingested.

It is a further object of the invention to provide an alternative composition, specifically a jelly, the use of which composition as an auxiliary means is to ease the taking of oral medication in solid form, which composition comprises iota-carrageenan as a jellifying agent and citric acid as a salivating agent, which composition does not require to be prepared for every active standard and every dosage of the active substance of the oral medication to be swallowed.

It is yet another object of the present invention to provide an alternative composition, specifically a jelly, the use of which composition as an auxiliary means is to ease the taking of oral medication in solid form, which composition comprises iota-carrageenan as a jellifying agent and citric acid as a salivating agent, which composition is cheaper to produce than known compositions according to the pre-amble.

It is yet another object of the present invention to provide an alternative composition, specifically a jelly, the use of which composition as an auxiliary means is to ease the taking of oral medication in solid form, which composition comprises iota-carrageenan as a jellifying agent and citric acid as a salivating agent, which composition obviates any further disadvantages of known auxiliary means, specifically a jelly, the use of which composition as an auxiliary means is to ease the taking of oral medication in solid form, which composition comprises iota-carrageenan as a jellifying agent and citric acid as a salivating agent.

SUMMARY OF THE INVENTION

One or more of the above-stated objects are achieved with a composition in the form of a jelly, comprising iota-carrageenan, citric acid and maltodextrin. In this composition iota-carrageenan acts as a jellifying agent and citric acid acts as a salivating agent.

One or more of the above-stated objects are achieved with a composition, specifically a jelly, the use of which composition as an auxiliary means is to ease the taking of oral medication in solid form, which composition comprises iota-carrageenan as a jellifying agent and citric acid as a salivating agent, characterized in one aspect of the invention in that the composition further comprises maltodextrin. The related technical advantage is that addition of maltodextrin improves the capability of the composition to keep the solid-form oral medication suspended when the latter is coated with the composition.

Preferably, the composition comprises maltodextrin in 1-4% in mass of the total mass of the composition. This offers the technical advantage of a sufficient long time before the solid-form oral medication will settle in the mouth. In a particular embodiment, the composition comprises maltodextrin in the range of 1.3-1.8% in mass of the total mass of the composition. Most preferably, the composition comprises maltodextrin in 1.5% in mass of the total mass of the composition. This offers the advantage of an optimum settling time and hence allow sufficient time for even people with very strong aversions to swallowing to swallow the solid-form oral medication that is suspended in the composition in the mouth.

The publication NL-1039241 (D1) discloses a jelly comprising iota carrageenan, citric acid and maltodextrin which is comprised in a salivating mix. The jelly can be used to coat solid medication before it is brought into the mouth. The jelly facilitates in taking oral medication in solid form. The maltodextrin comprised in the salivating mix is calculated to amount to 1.14% in mass of the total mass of the composition.

The present invention signifies a selection invention over the disclosure of D1, in particular in regard of the aspect of yield stress. The yield stress is the force or stress required to break down the viscosity of the composition, allowing solid medication to separate from the layer of (jelly) composition enclosing it. The higher the yield stress, the more effective the (jelly) composition is in its described function. Data of comparative tests are described later in relation to FIGS. 6-7. This data substantiates the technical advantages of the addition of maltodextrin as mentioned above.

The present invention signifies that not only the viscosity of the jelly composition is important, but that the visco-elastic behaviour thereof is important too. It is known from prior art that a carrageenan gel shows visco-elastic behaviour. However, what was not known until now was that polymer-like structures such as those of starch and starch derivatives such as maltodextrin influence the yield stress in a way as to unexpectedly increase the same.

According to another aspect of the invention, the composition comprises citric acid in 0.05 to 0.10% in mass of the total mass of the composition. The related technical advantage is that the citric acid imparts a neutral to slightly acidic taste to the composition, which range of tastes are acceptable to most people using oral medication.

Preferably, the composition comprises citric acid in the range of 0.05-0.1% in mass, and more preferably 0.06% in mass, of the total mass of the composition. The related technical advantage is that the pH of the composition can be regulated to lie in the range of 4.8-6.5, more preferably in the range of 5.0-6.0, and most preferably for the pH to be 5.5.

According to yet another aspect of the invention, the composition comprises a calcium sequestrant. The related technical advantage is that this sequestrant aids in adjusting the pH of the composition. Another related technical advantage is that this sequestrant also aids in adjusting the Ca-ion activity in the composition. A certain amount of Ca-ion activity is beneficial in order to maintain a desired viscosity of the composition during its production and also during use thereof, i.e. in the mouth.

In and of itself the use of calcium in carrageenan jellies is known from the prior art. For example according to publication JP 2003/104912 (D2) calcium ions are used as a coagulation inhibitor. The disclosure relates to $Ca^{2+}$-containing ionic matter in an amount of 0.01-10 times (by weight) the amount of carrageenan in the composition. Also, it is disclosed in publication US 2007/128285 (D3) that the inclusion of water-soluble salts of metal ions such as a calcium or potassium ion (e.g. the inorganic acid salts such as chloride, phosphate or of sulphuric acid, or organic acid salts such as of lactic acid or citric acid) into the composition is effective in order to jellify the composition and enhance the jelly stability.

A calcium sequestrant provides calcium ions. While not intending to be bound by any theory, the inventor believes that the calcium ions, as indeed other divalent metal ions, strengthen the structure of the jelly due to the calcium forming ionogenous bridges between carrageenan molecules by way of its sulphate group. In addition to calcium chloride, other calcium sequestrants are, inter alia, calcium carbonate and calcium oxide. Addition of calcium carbonate to a composition according to the invention will increase the pH, so a skilled person will contemplate the addition of citric acid in order to lower the pH to a desirable value of 4.8-5.8. All alternatives will, of course, be subject to compatibility with health regulations relating to the use of a composition as an auxiliary means to ease the taking of oral medication in solid form, and as such may require workshop modifications by a skilled person.

The aspect of inclusion of a calcium sequestrant in a composition comprising iota-carrageenan, citric acid and maltodextrin according to the invention signifies novelty and an inventive step over the disclosures of D2 and D3 in light of the disclosure of D1. D2 discloses the use of calcium ions as a coagulation inhibitor and D3 discloses the use of calcium ions as a jellifying agent. Inclusion of a calcium sequestrant affords a higher yield stress of the composition. The higher the yield stress, the more effective the composition (jelly) is in its described function. Data of comparative tests with and without calcium chloride are described later in relation to FIGS. 8-9. This data substantiates the technical advantages of the inclusion of a calcium sequestrant as mentioned above.

The composition comprises an amount of a calcium sequestrant such that the Ca-ion activity of the composition is <500 ppm. Preferably, the composition comprises an amount of a calcium sequestrant such that the Ca-ion activity of the composition is between 10 ppm and 100 ppm. More preferably, the composition comprises an amount of a calcium sequestrant such that the Ca-ion activity of the composition is between 20 ppm and 80 ppm.

Preferably, the calcium sequestrant comprised in the composition is a salt of citric acid. This is advantageous as the composition already needs to comprise citric acid in order to impart a neutral to slightly acidic taste to the composition. The amount of citric acid required will be as much as is needed to hold the pH between 4.8 and 5.8. In practice, the amount of citric acid to be added will be in the order of magnitude of 0.05-0.1% in mass of the total mass of the composition. Without intending to be bound by any theory, the inventor offers the following explanation. During production of iota carrageenan, potassium hydroxide is used for adjusting the pH. Use of this iota carrageenan for the composition of the invention leads to ca. 3000 ppm of potassium being comprised in the composition. So upon addition of citric acid, in first instance potassium citrate will be formed and calcium will bond to the sulphate groups of the iota carrageenan until all potassium has bonded. It should clear that the use of iota carrageenan from a different source may lead to a different amount of potassium, or an equivalent, being comprised in the composition, and to a slight variation in the amount of citric acid needed to hold the pH between 4.8 and 5.8.

Also preferably, and as an alternative, the calcium sequestrant comprised in the composition is calcium chloride. This offers the advantage of a readily available and cheaper alternative sequestrant. Preferably, the amount of calcium chloride comprised in the composition is lower than 0.4% in mass relative to the total mass of the composition. More preferably, the amount of calcium chloride comprised in the composition lies in the range of 0.0-0.2% in mass relative to the composition. Most preferably, the amount of calcium chloride comprised in the composition is 0.005%-0.015% in mass relative to the total mass of the composition. This offers the technical advantage of tailoring the shelf-life of the composition according to varying requirements.

DETAILED DESCRIPTION OF THE INVENTION

The composition according to the invention is qualified as universal because it can be used for the intake of any type of medication that can appropriately be taken orally. In particular, this composition is suited for facilitating the swallowing and oral administration of solid-form medication, especially in the form of pills, tablets, capsules and powders.

The composition according to the invention does not contain any active therapeutic or prophylactic substance and thus can be used with all medication in solid form, whatever the unitary form, dosage or active substance it might comprise.

According to one embodiment of the composition, it is provided in the form of a jellified paste that develops its lubricating properties when it comes into contact with saliva and/or the mucosal membrane in the mouth. These properties are enhanced by the presence of a salivating agent. The composition according to the invention can be used to facilitate the intake of medication, for example after mingling the composition and the medication on a spoon and bringing it into the mouth. The medication can be used in its galenical, commercial form, as available in pharmacies. In practice, during the intake of medication, the composition takes the place of water which is generally used for swallowing capsules, pills, tablets or powders. The composition according to the invention is in particular intended for people, especially children and elderly persons, who suffer from medication-intake problems, and for people suffering from dysphasia and/or xerostomia.

The composition according to the invention can be used to coat solid-form medication, especially in the form of a tablet, pill, capsule or powder, before it is brought into the mouth. No manipulation or modification of the medication in the form of a tablet, pill, capsule or powder is required. The tablet, pill, capsule or powder is simply placed in a sufficient quantity of composition, in order for the latter to coat the former. The composition according to the invention is brought together with the medication in the form of a tablet, pill, capsule or powder entirely in an intact form, without any modification of this medication, such as through grinding of the pill or tablet, or opening of the capsule. Bringing the composition and the medication together can be done by the patient himself, just before introducing the medication into the mouth. The pill, tablet, capsule or powder, in its commercialized form, is taken up in the composition according to the invention. Just before the intake, the medication in an independent unitary form is placed in the composition according to the invention, and then brought into the mouth. The medication in the form of a pill, tablet or capsule, can also be brought into the mouth in a separate way, before or after introducing the composition in the mouth. For example, it is possible to place the medication directly in the mouth and to take the composition subsequently, in the same way as using water. In particular, no opening of capsules, or crushing of pills or tablets required if the medication is incorporated in its intact form in the composition according to the invention, before or after introduction in the mouth.

According to one embodiment of the invention, the composition comprises citric acid. One of its functions is to act as a salivating agent. Another of its functions is to impart a neutral to slightly acidic taste to the composition. Alternatively, one or several other compounds stimulating saliva-production in the mouth can replace citric acid either entirely or in part to the extent of its amount in the composition. An example of an alternative is ascorbic acid.

According to a further embodiment, citric acid is comprised in the composition in an amount of 0.05-0.10% in mass, preferably 0.05-0.08% in mass and most preferably 0.06% in mass, relative to the total mass of the composition.

According to yet another embodiment, the composition comprises an amount of citric acid such as to obtain a pH that lies in the range of 4.8-6.5, preferably 5.0-6.0 and most preferably 5.5.

According to another embodiment, the composition comprises iota-carrageenan in an amount of 0.5-2.0% in mass, preferably 0.7-1.0% in mass, relative to the total mass of the composition.

Carrageenans are linear sulphated polysaccharides that are often extracted from red seaweeds. It may be a carrageenan of the molecular structure types $\alpha$, $\beta$, $\gamma$, $\theta$, $\lambda$, $\mu$, $\sigma$, $\upsilon$, $\iota$, or $\kappa$. Carrageenans are commercially available in the form of kappa ($\kappa$), iota ($\iota$) or lambda ($\lambda$). In the present invention, the iota ($\iota$) form is used. The iota form is often derived from *Eucheuma spinosum*. An advantage of the iota-carrageenan is that it is thixotropic. The presence of this jellifying agent imparts a naturally pleasant and appetizing character to the composition while it also serves the function of lubricating the upper respiratory tract (mouth, pharynx and larynx) and subsequently the oesophagus. When the composition is present in the mouth and it is in contact with saliva, it immediately reacts as a lubricating substance. The presence of a salivating substance, especially on the basis of citric acid, induces hyper-salivation that further contributes to ease of swallowing.

It is possible to use another jellifying agent in combination with the iota-carrageenan. This jellifying agent can be another polysaccharide, for example cellulose or agar. The jellifying agent should be present in such an amount in the composition that its mass percentage relative to the total mass of carrageenan is less than 50%, preferably less than 30% and more preferably less than 10%, in order to prevent it from modifying the rheological properties of the composition. According to one embodiment, iota-carrageenan is the only jellifying agent comprised in the composition.

According to another embodiment, the composition has a certain visco-elasticity. In particular, the measuring of the visco-elastic components, storage G' and loss G" relative to the frequency of deformation of jellies according to the invention (measured, for example, with a Rhéolab MCR 301 from Anton Paar at a constant amplitude of 1% at 22° C.) shows that the storage modulus G' is greater than the loss modulus G". The relation between the two modules (G' and G") expressed as the formula tangent delta=G"/G' is preferably always less than 1 for a range of frequencies between 0.1 and 100 s-1 equally. In particular, the tangent delta is between 0.10 and 0.65. Moreover, the value of the tangent delta increases, in an advantageous manner relative to the increase of the frequency. Such visco-elastic properties determine the formation of the composition as a stable elastic substance. These properties are obtained due to the presence of iota-carrageenan in a sufficient amount.

DESCRIPTION OF THE DRAWINGS

The above and further preferred embodiments and technical advantages of the invention will now be described, by way of example, with reference to the accompanying drawings in which:

FIGS. 1-3 depict the mechanical spectrum (values of G' and G" relative to the frequency of deformation) of compositions comprising various types of carrageenan in an amount of 2% in mass relative to the total mass of the composition. These Figures illustrate the differences between the storage modulus G' and the loss modulus G" relative to the frequency for the various compositions.

FIG. 1 relates to a composition comprising kappa-carrageenan. It reveals that the storage modulus G' is greater than the loss modulus, G". The difference between G' and G" is not stable relative to the frequency, which means that the composition is very fragile.

FIG. 2 relates to a composition comprising lambda-carrageenan. It reveals that there is no notable difference between the storage modulus G' and the loss modulus G". This is an expected outcome because this composition does not jellify.

FIG. 3 relates to a composition comprising iota-carrageenan. It reveals that the storage modulus G' is much greater than the loss modulus G". The difference between the two modules (G' and G") remains steady in the whole range of frequencies, which means that there is a formation of a composition with a stable elastic component.

FIG. 4 depicts the mechanical spectrum (values of G' and G" relative to the frequency of deformation) of a composition comprising iota-carrageenan in an amount of 0.7% in mass relative to the total mass of the composition. It reveals a stable jellified condition even at higher frequencies.

FIG. 5 depicts the mechanical spectrum (values of G' and G" relative to the frequency of deformation) of a composition comprising iota-carrageenan in an amount of 0.5% in mass plus cellulose in an amount of 0.2% in mass, both relative to the total mass of the composition. It reveals that there is no jellified condition at higher frequencies.

Figure 1:
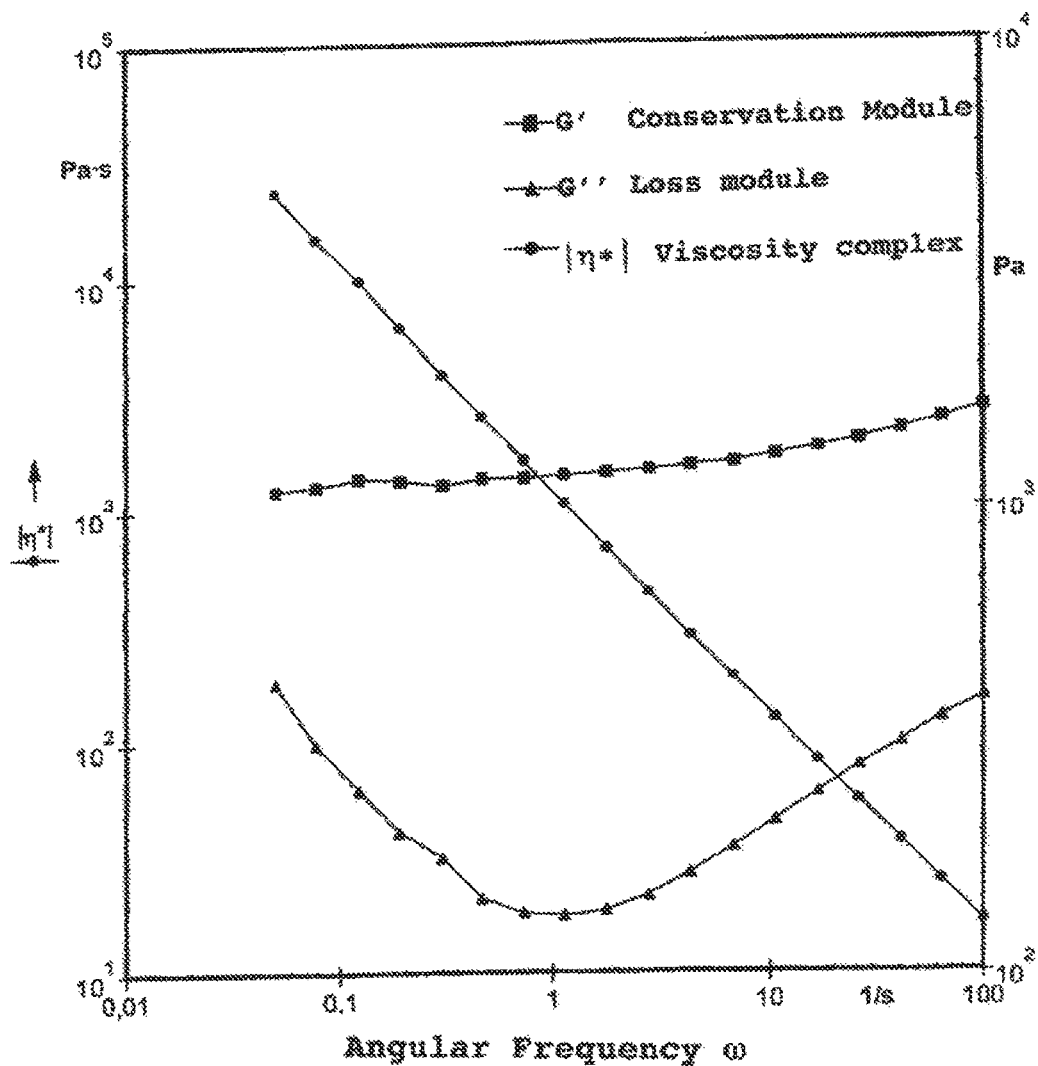
FIGS. 1-5 depict the mechanical spectrum (values of G' and G" relative to the frequency of deformation) of compositions that comprises different types of carrageenan in different amounts relative to the total mass of the composition.
Figure 2:
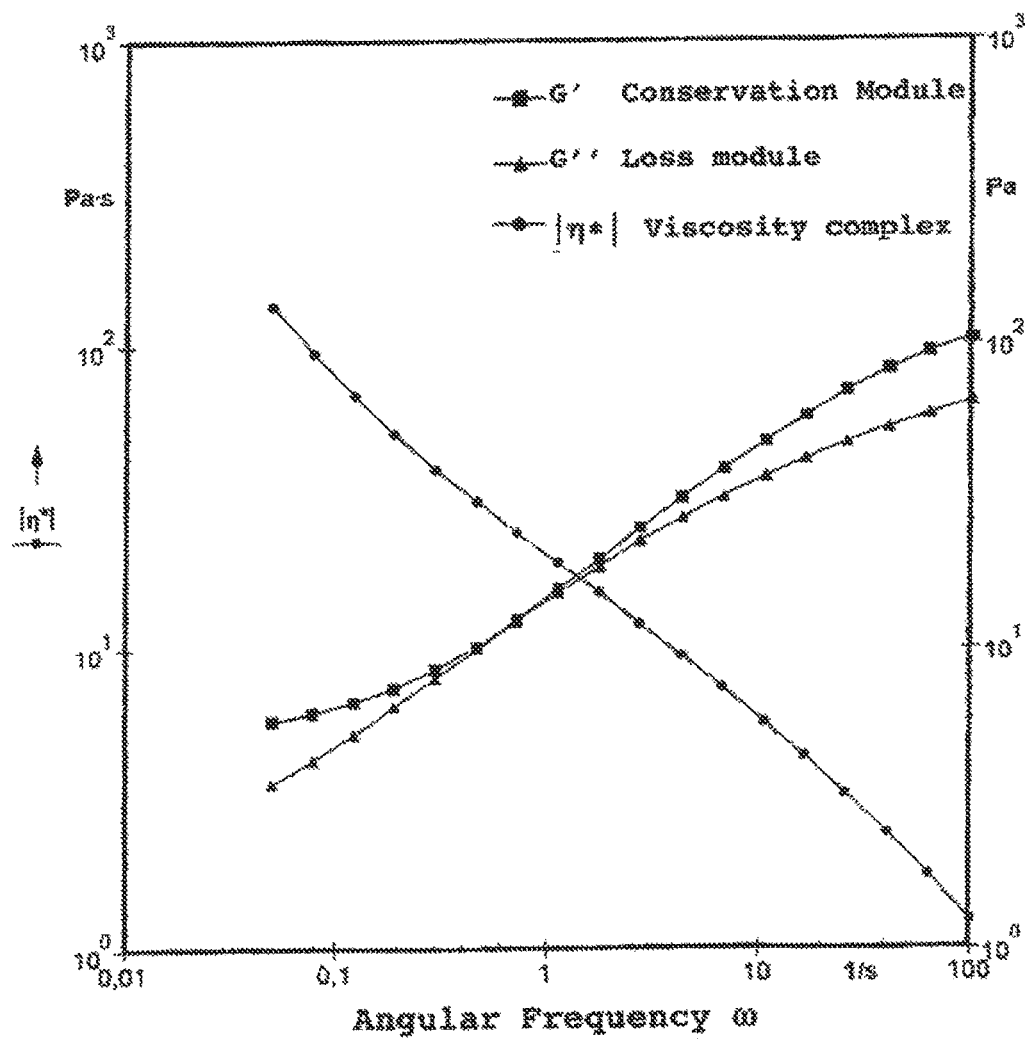
Figure 3:
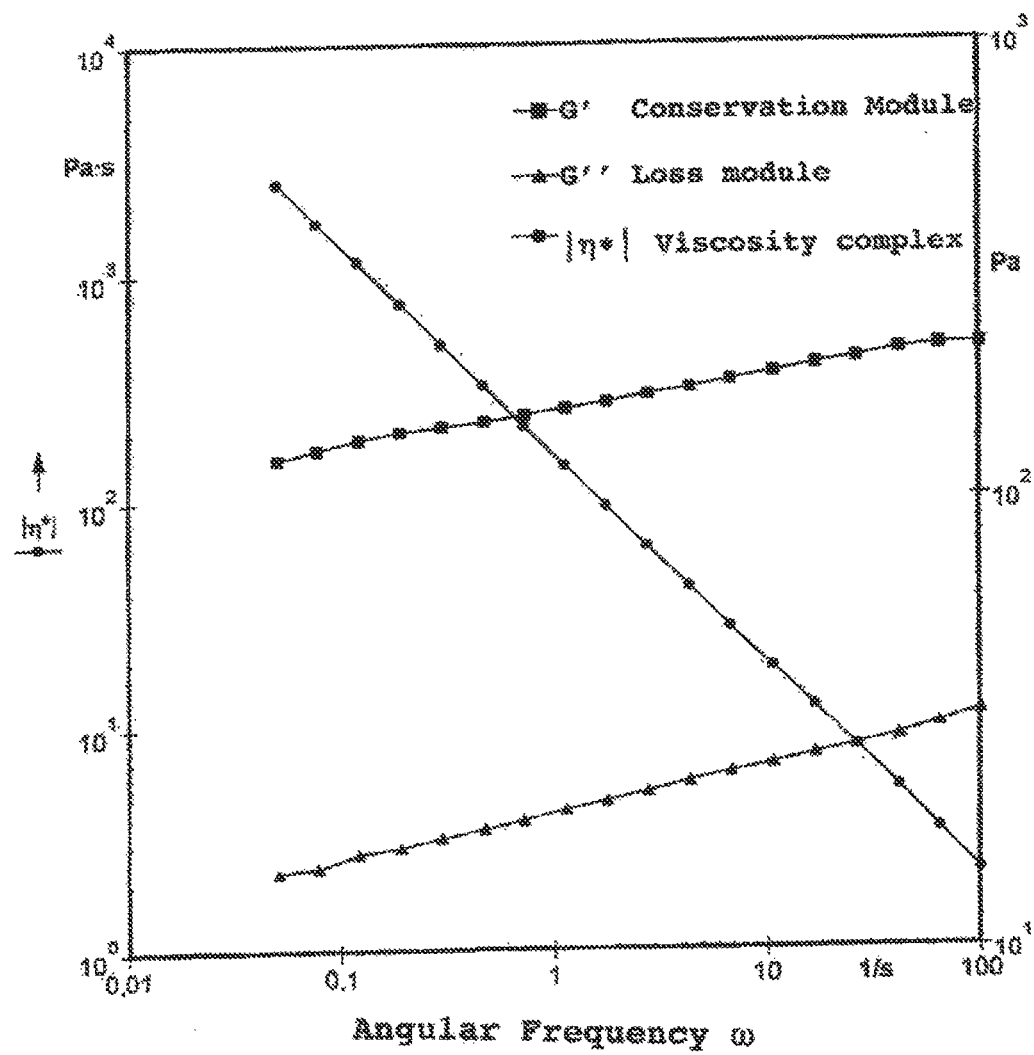
Figure 4:
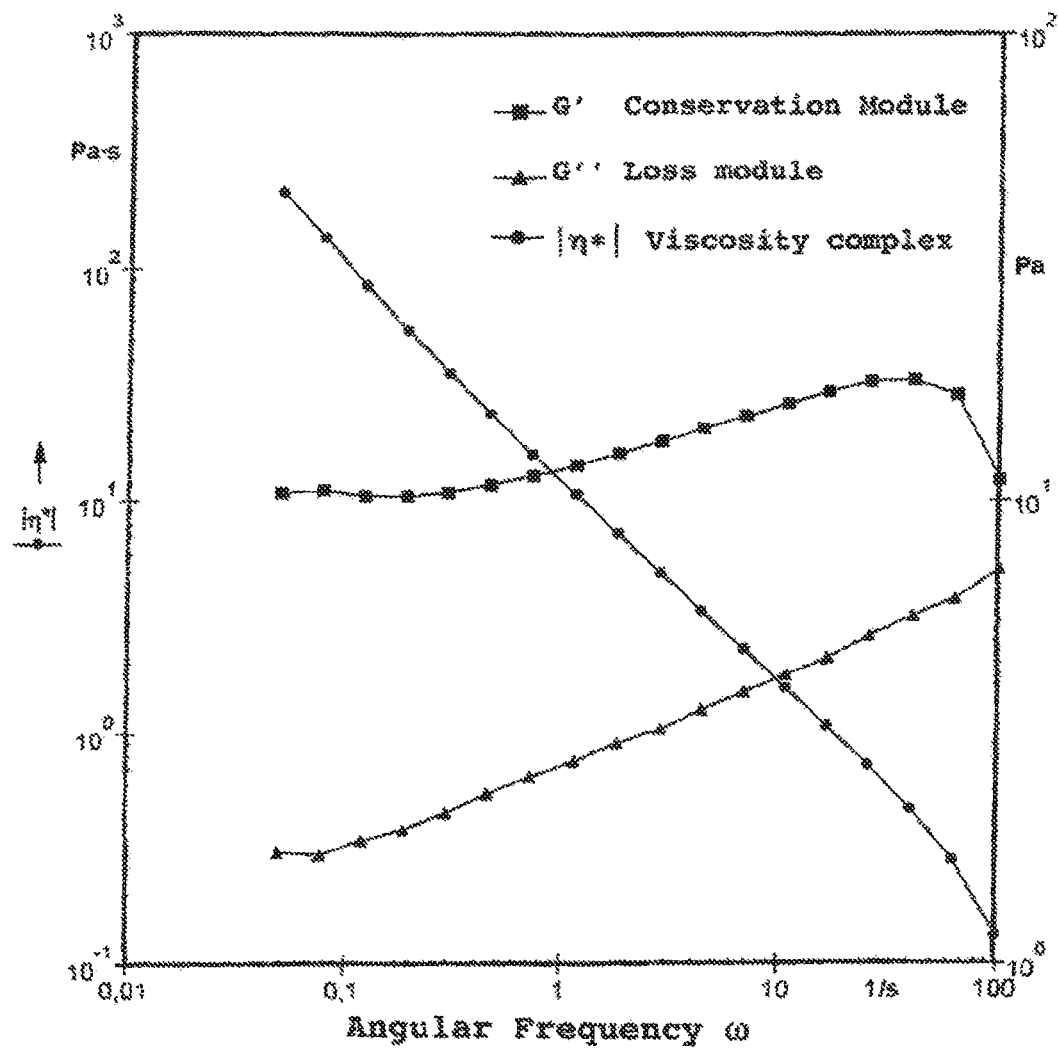
Figure 5:
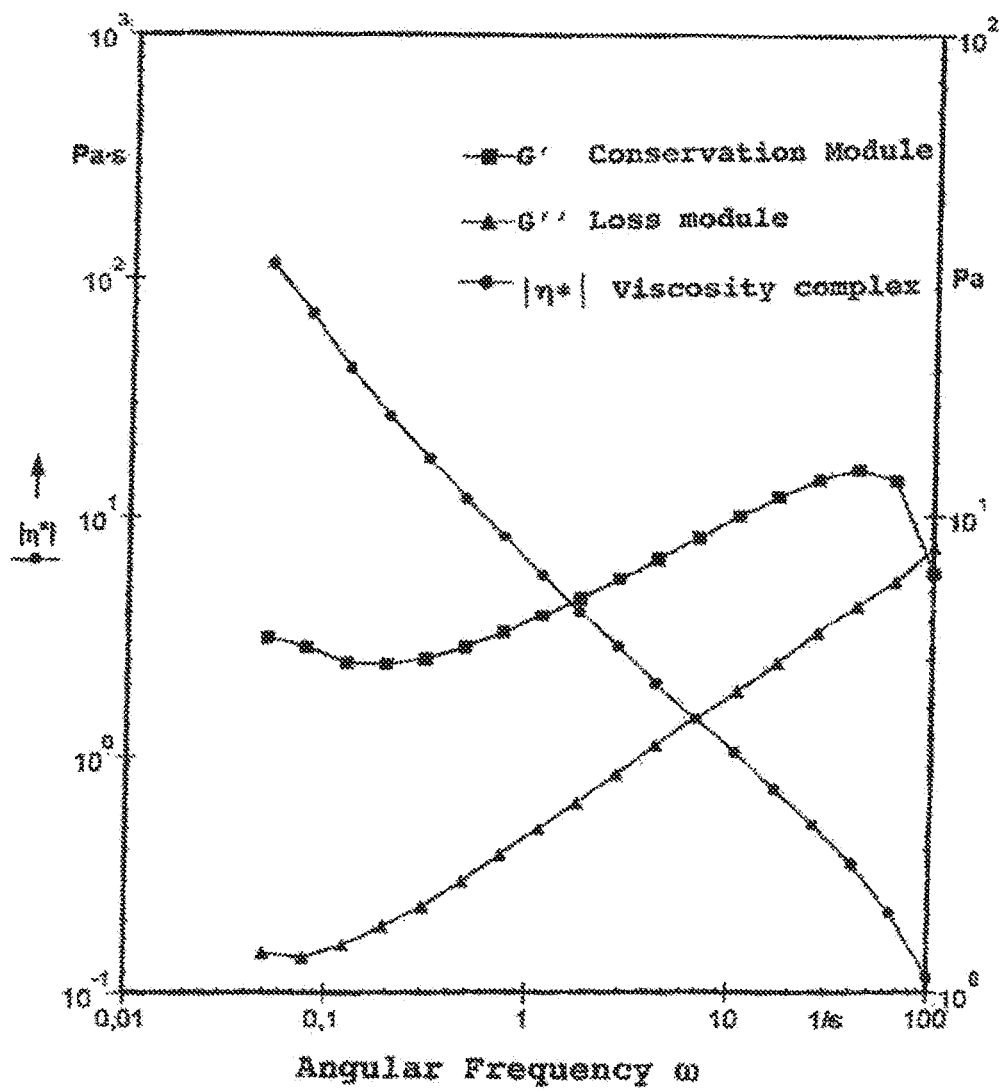

According to FIGS. 4 and 5, the composition comprising iota-carrageenan in an amount of 0.7% in relative mass has a tangent delta varying from 0.6 to 0.17 and it thus provides a jellified structure at all frequencies. For the composition comprising iota-carrageenan in an amount of 0.5% in relative mass and cellulose in an amount of 0.2% in relative mass, the average tangent delta varies from 1.12 to 0.25, which means that the composition provides a non-jellified structure at higher frequencies. The addition of cellulose to a composition comprising iota-carrageenan in an amount of 0.7% in relative mass does not guarantee a jellified structure at higher frequencies.

Figure 6:
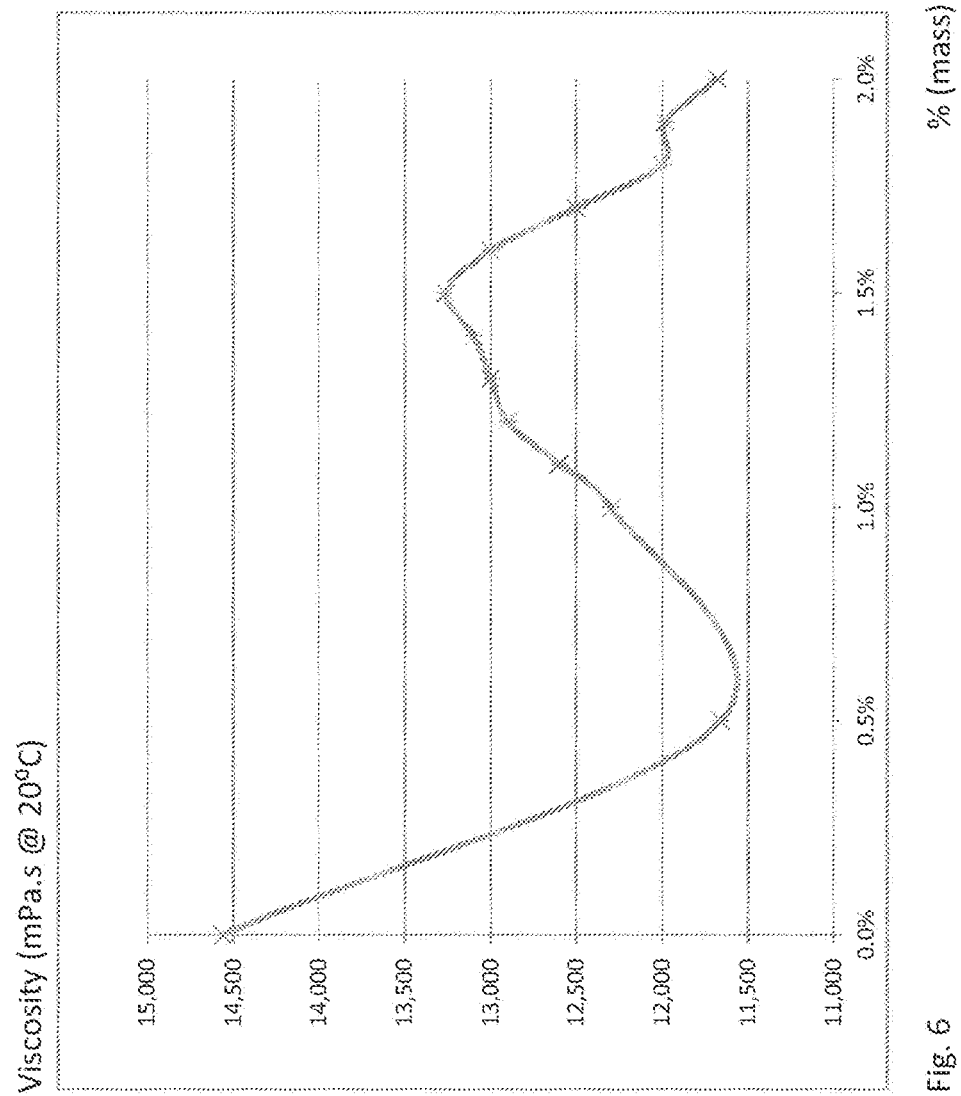
FIGS. 6-7 depict the results of comparative tests of some compositions according to the invention in regard of viscosity and the yield stress, respectively, as a function of the amount and the nature of maltodextrin present in the composition.
Figure 7:
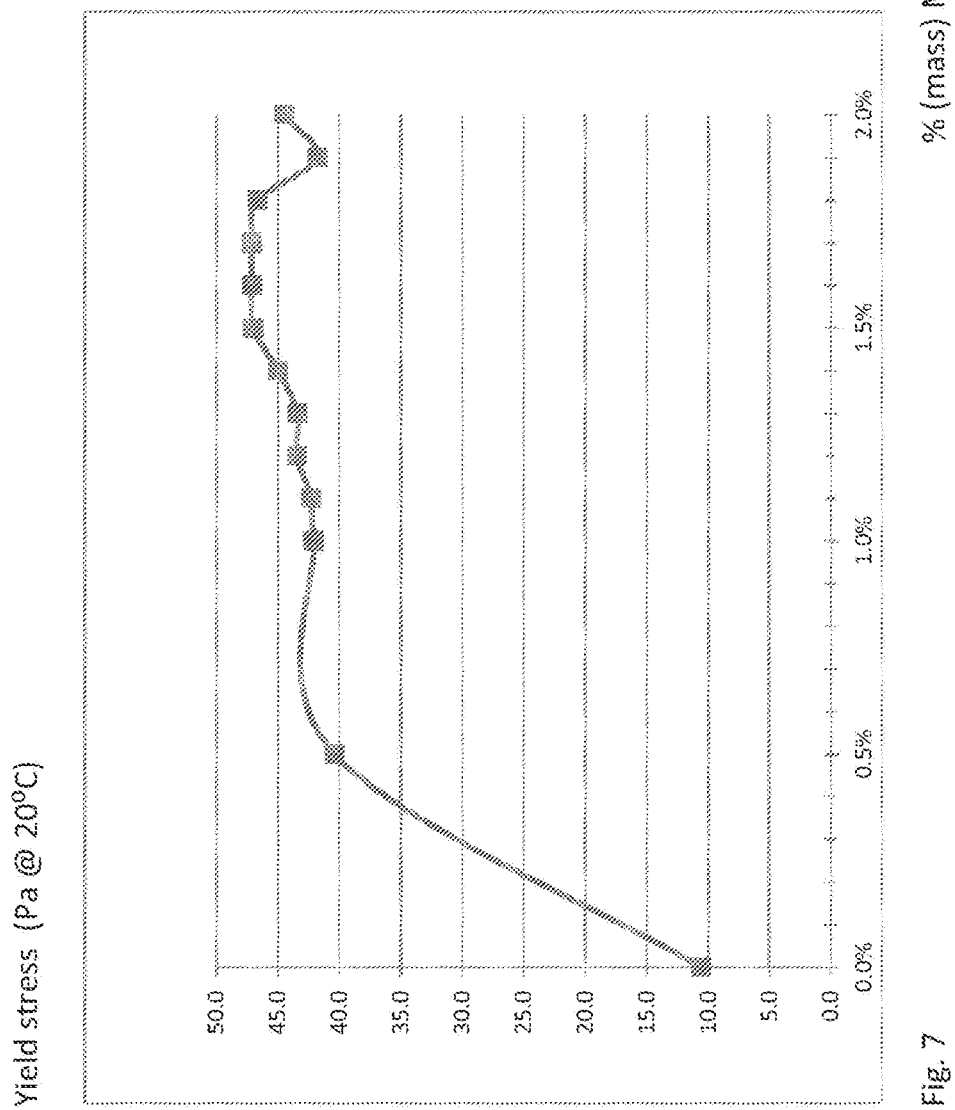

FIGS. 6 and 7 depict the results of comparative tests of some compositions according to the invention in regard of viscosity and the yield stress, respectively, as a function of the amount and the nature of maltodextrin present in the composition.

The yield stress of the tested compositions was made through the use of a controlled-stress rheometer, in this instance a Brookfield DX3TRVT Rheometer. This type of instrument makes use of a controlled stress ramp to gradually increase the amount of force on the sample until flow is initiated. For this comparison the variable was the amount of maltodextrin in the composition. The composition comprised the following:

water: balance
iota-carrageenan: 0.800%
aspartame: 0.055%
citric acid: 0.070%
maltodextrin: 0.00 to 2.00%
potassium sorbate: 0.800%
calcium chloride: 0.005%

The measurement results are:

| % (mass) maltodextrin | yield stress (Pa @ 20° C.) | viscosity (mPa · s @ 20° C.) |
|---|---|---|
| 0.0 | 10.6 | 14,560 |
| 0.5 | 40.4 | 11,660 |
| 1.0 | 42.1 | 12,300 |
| 1.1 | 42.3 | 12,600 |
| 1.2 | 43.5 | 12,900 |
| 1.3 | 43.4 | 13,000 |
| 1.4 | 45.0 | 13,100 |
| 1.5 | 47.0 | 13,260 |
| 1.6 | 47.1 | 13,000 |
| 1.7 | 47.1 | 12,500 |
| 1.8 | 46.7 | 12,000 |
| 1.9 | 41.8 | 11,980 |
| 2.0 | 44.5 | 11,680 |

FIG. 6 shows the viscosity of a composition as a function of the percentage (in mass) of maltodextrin in the composition. The viscosity is seen to have a clear build up around an optimum at 1.5%.

Measurement of the yield stress of the test compositions reveal a surprising relationship with the amount of maltodextrin in the composition. FIG. 7 shows that the yield stress increases with an increase in the amount of maltodextrin, with an optimum in the range of approx. 1.3-1.8%.

In stark contrast, the composition of D1, comprising Salivating Mix (Firmenich) that in turn comprises maltodextrin in an amount calculated to be approximately 1.14% by mass, has a yield stress of 5 Pa.

A possible explanation of a nearly eight-fold increase of the yield stress of a composition according to the invention in comparison with the yield stress of a composition according to D1 is as follows. Salivating Mix (Firmenich) comprises five components: two tintling agents, citric acid, maltodextrin and modified starch. As shown in FIGS. 6-7, a composition comprising carrageenan but no maltodextrin has a lower yield stress than a composition comprising a certain amount of maltodextrin.

Figure 8:
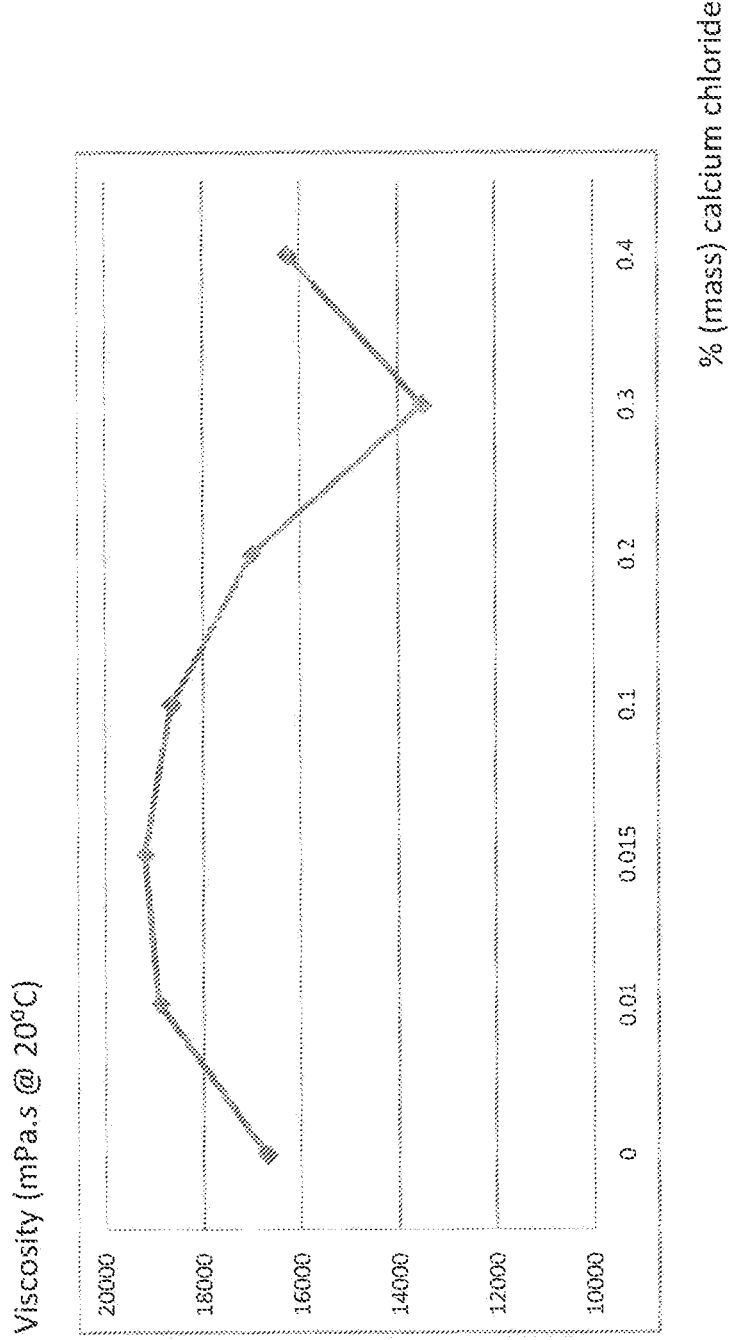
FIGS. 8-9 depict the results of comparative tests of some compositions according to the invention in regard of viscosity and the yield stress, respectively, as a function of the amount and the nature of calcium present in the composition.
Figure 9:
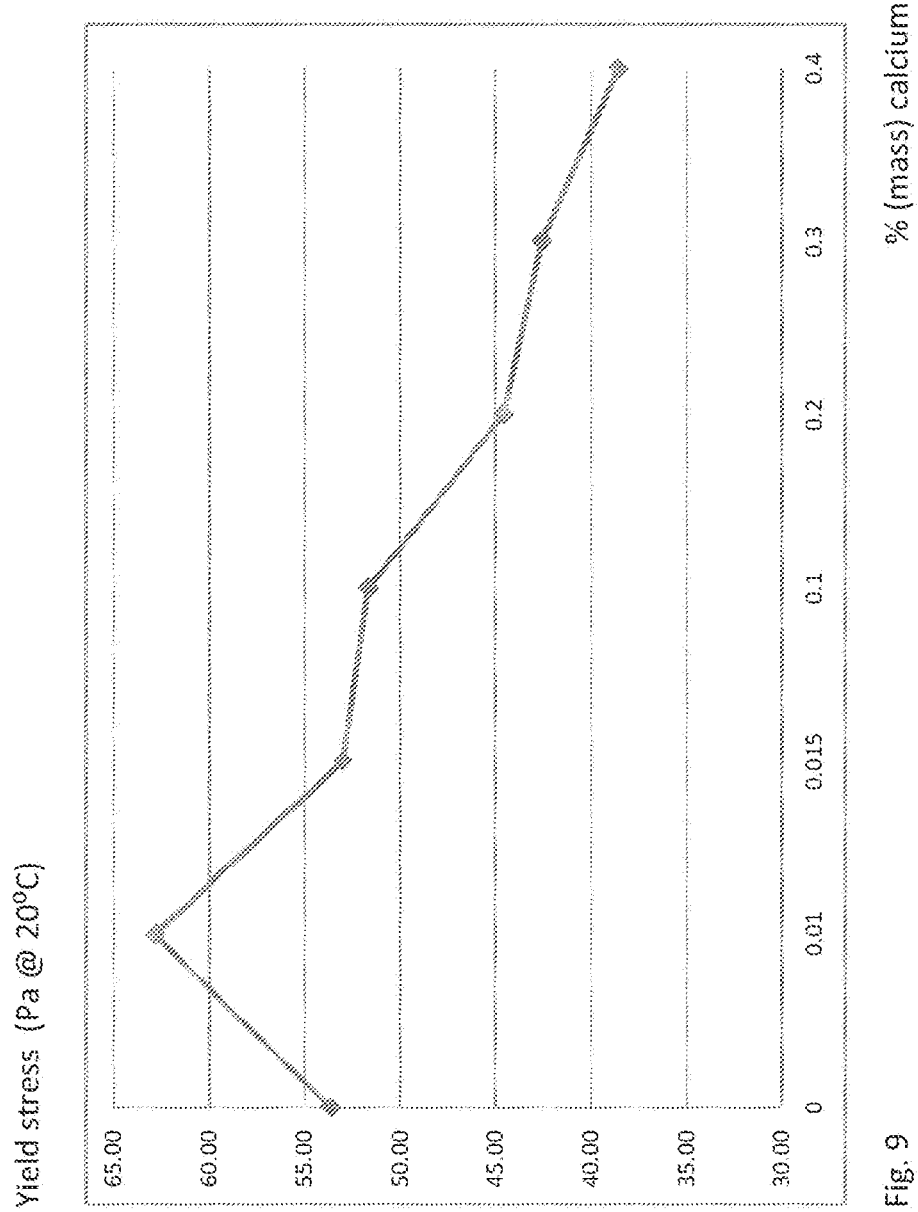

FIGS. 8 and 9 depict the results of comparative tests of some compositions according to the invention in regard of viscosity and the yield stress, respectively, as a function of the amount and the nature of calcium present in the composition.

It was not known until now what effect, if any, calcium chloride has on the yield stress of the composition. A series of compositions were tested, whereby the amount of maltodextrin was held at the optimum value of 1.5% in mass (as based on results shown in FIGS. 6 and 7) and the amount of calcium chloride was varied between 0.0% and 2.0% in mass.

The composition comprised the following:
water: balance
iota-carrageenan: 0.800%
aspartame: 0.055%
citric acid: quantity sufficient to hold the pH at 4.8-5.8, in practice ca. 0.05-0.1%
maltodextrin: 1.50%
potassium sorbate: 0.800%
calcium chloride: 0.0-2.0%
The measurement results are:

| % (mass) calcium chloride | yield stress (Pa @ 20° C.) | viscosity (mPa · s @ 20° C.) |
|---|---|---|
| 0.0 | 53 | 16,700 |
| 0.01 | 63 | 18,900 |
| 0.015 | 53 | 19,200 |
| 0.1 | 52 | 18,650 |
| 0.2 | 45 | 17,000 |
| 0.3 | 43 | 13,500 |
| 0.4 | 39 | 16,250 |

In regard of both the viscosity and the yield stress an optimum is revealed in the range of 0.0-0.4% in mass of calcium chloride. Most preferably, the amount of calcium chloride comprised in the composition is 0.01% in mass relative to the total mass of the composition. The results are depicted in FIGS. 8-9.

A possible explanation of a relatively low viscosity of a composition comprising ca. 0.3% in mass of calcium chloride may lie in the formation of calcium citrate and there not being sufficient free calcium ions for matrix formation with electrostatic or ionic forces acting between the carrageenan molecules. Reference is made to the explanation given above that upon addition of citric acid, in first instance potassium citrate will be formed and calcium will bond to the sulphate groups of the iota carrageenan until all potassium has bonded The fact remains that with the addition of calcium chloride according to the tested embodiments, the viscosity is at least the level of 12,000 mPa·s @ 20° C. with the above-described surprising, approximately eight-fold increase in the yield stress of the composition (ca. 40 Pa or higher @ 20° C.) as compared with the yield stress of a composition according to prior art D1 (5 Pa @ 20° C.).

Alternatives for calcium chloride as a calcium sequestrant are, inter alia, calcium carbonate and calcium oxide. Addition of calcium carbonate to a composition according to the invention will increase the pH, so a skilled person will contemplate the addition of citric acid in order to lower the pH to a desirable value in the range of 4.8-5.8. All alternative calcium sequestrants will, of course, be subject to compatibility with health regulations relating to the use of a composition as an auxiliary means to ease the taking of oral medication in solid form, and as such may require workshop modifications by a skilled person.

DETAILED DESCRIPTION OF FURTHER EMBODIMENTS AND EXAMPLES

According to one aspect of the invention, a just balance needs to be struck between the pourability of the composition and its viscosity. It is presumed that in the throat of a person taking oral medication, the composition should flow easily but not so easily as to flow into the person's windpipe. Therefore, it is desired that the composition has a suitable texture, not too short and not too long, so that when pouring the composition it can just stop short of continuing as a thread. Additionally, it is desirable that the composition preferably has a non-sticky and otherwise only a very slight sticky mouthfeel considering that a composition sticking to the palate will induce repeated swallows. Of course, the mouthfeel should not be more than just very slightly sticky because repeated strong swallows after the first swallow may cause discomfort, and may in certain circumstances even be dangerous, to some dysphagia patients.

During the course of producing and using the composition according to the invention as an auxiliary means in easing the taking of oral medication in solid form, it has been found that iota-carrageenan provides for a stable viscous network that does not exhibit too sticky properties, and that it provides for the most prolonged storage stability over time. Stability in the present context means that the composition does not show phase separation (e.g. aggregation, syneresis or precipitation). The absence of starch in the composition according to the invention is an important feature considering that starch renders the composition sensitive to breakdown by amylase from the saliva of dysphagia patients, thus decreasing the stability (of the viscosity) of the composition.

According to another aspect of the invention, phase separation, i.e. the formation of layers and changes in viscosity during storage of the composition are unwanted. A possible problem may lie in the formation of calcium-acid complexes, resulting in salt precipitates. To avoid such problems, calcium sequestrants, for example calcium chloride, or a salt of citric acid, are comprised in the composition in order to adjust the pH and also in order to adjust Ca-ion activity in the composition. A certain amount of Ca-ion activity is beneficial in order to maintain a desired viscosity of the composition during its production and its later use. The presence of calcium ions helps the polymers in the composition to re-arrange themselves around the calcium ions. The calcium ions also allow for a better orientation of the carrageenan molecules in the composition. Preferably, Ca-ion activity is between 10 ppm and 100 ppm, more preferably between 20 ppm and 80 ppm. To prevent the formation and precipitation of insoluble calcium salts in time, calcium sequestrants should however be dosed with care. In general, the less the better, as evidenced by the results shown in FIG. 9. When calcium chloride is the calcium sequestrant, the preferred amount thereof in the composition is 0.005% in mass of the total mass of the composition.

A possible alternative solution to avoidance of phase separation of the composition of the invention lies in the use of anionic (water-)soluble fibres. Anionic (water-) soluble fibres can bind calcium and thus aid in optimizing the pH of the composition, and they can aid in increasing the viscosity of the composition. As such, examples of anionic (water-) soluble fibres are well known to the person skilled in the art.

According to an embodiment of the composition according to prior art D1, the composition comprises water in an amount of 80-99% in mass, preferably 84-97% in mass, relative to the total mass of the composition. The choice of the amount of water, in combination with the nature and the amount of iota-carrageenan, and optionally an amount of an additional jellifying agent, allows for adjustment of the viscosity of the composition. The composition according to the invention has a viscosity of 500-4,500 mPa·s, and preferably 700-2,000 mPa·s, as measured with a Physica MC1 Rheometer from Anton Paar (measurement at 1 min 20 rpm at 22° C.). It is pointed out that measurement of the viscosity of the embodiments mentioned above was done using a different type of rheometer (Brookfield DX3TRVT) and at a different temperature. For embodiments of the composition according to the invention, a target value for the viscosity is approx. 6,000-10,000 mPa·s, and preferably higher, at 20° C. as measured using a Brookfield Rheometer (1 min spindle 4 at 20 rpm).

According to a further embodiment of the present invention, the composition comprises a preservating agent. Examples of a suitable preservating agent are potassium sorbate and sodium benzoate. Preferably, the preservating agent is potassium sorbate, comprised in an amount of 0.2-1.0% in mass, more preferably comprised in an amount of 0.4-0.8% in mass, and even more preferably in an amount of 0.6-0.8% in mass, relative to the total mass of the composition.

According to a further embodiment, the composition comprises a flavouring agent, preferably for orange, lemon, lime, red fruit (e.g. cherry and strawberry) or mint flavours. The flavouring agent is comprised in an amount of 0.05-0.20% in mass, preferably in an amount of 0.07-0.10% in mass, relative to the total mass of the composition.

According to a further embodiment, the composition comprises a sweetening agent chosen from the group of: saccharose, aspartame, sucralose, *stevia*, inuline and derivatives thereof. For example, if the sweetening agent is saccharose, then it should be comprised in the composition in an amount of 15-20% in mass, preferably 12-13% in mass, relative to the total mass of the composition. If the sweetening agent is aspartame, then it should be comprised in the composition in an amount of 0.03-0.06% in mass relative to the total mass of the composition.

According to one specific embodiment, the composition according to the invention comprises (all amounts in mass % relative to the total mass of the composition):

| | |
|---|---|
| iota-carrageenan | 0.5-2%, preferably 0.7-1.0% |
| citric acid | 0.05-0.10%, preferably 0.05-0.08% |
| maltodextrin | 1.0-2.0%, preferably 1.3-1.8% |
| potassium sorbate | 0.4-0.8%, preferably 0.6-0.8% |
| saccharose | 15-20%, preferably 12-13% |
| flavouring agent | 0.05-0.20%, preferably 0.07-0.10% |
| water | approximately 80-90%, for example |

According to another embodiment, the composition according to the invention comprises (all amounts in mass % relative to the total mass of the composition):

| | |
|---|---|
| iota-carrageenan | 0.5-2.0%, preferably 0.7-1.0% |
| citric acid | 0.05-0.10%, preferably 0.05-0.08% |
| maltodextrin | 1.0-2.0%, preferably 1.3-1.8% |
| potassium sorbate | 0.4-0.8%, preferably 0.6 to 0.8% |
| aspartame | 0.03-0.06% |
| flavouring agent | 0.05-0.20%, preferably 0.07-0.10% |
| water | approximately 95-99%, for example 98% |

According to another embodiment, the composition according to the invention is characterized by the absence of one or more of hydroxypropyl methylcellulose, gelatin, spilanthol, jambu oleoresin and agar.

According to another embodiment, the composition according to the invention is characterized by the absence of one or more of carob, carboxymethyl cellulose and xanthan gum.

BEST MODE OF THE INVENTION

A composition according to the invention can be prepared in a simple way, by dissolving the iota-carrageen in water at a temperature of around 60° C. The other components to be comprised in the composition can be added during the formation of the composition when it is still hot, or when the composition is at room temperature, this depending on the heat-resistance and the solvability of such components in the composition.

A non-limitative example of production of the composition is given below. The production steps are roughly as follows: Weigh the water and the potassium sorbate in a beaker, then heat up to 60° C. while stirring with a magnetic stirrer. If a colouring agent is required, then it should be added at this stage. Next, weigh the jellifying agent in a beaker. When the water is at the right temperature and the potassium sorbate has completely dissolved, place the beaker in a turbine and start agitating at 700 rpm. Then add the jellifying agent to the contents of the beaker and increase agitation to the rate of 1,500 rpm. Carry on agitating for 20 minutes. When the composition is back at room temperature, weigh the maltodextrin, the citric acid, and the calcium sequestrant and add these to the contents of the beaker. Continue agitating the contents and add any desired flavouring agent.

The present invention thus provides a composition, specifically a jelly, the use of which is to ease the taking of oral medication in solid form, and to the use of such a composition as an auxiliary means for the stated purpose. The invention relates in one aspect to a composition, specifically a jelly, the use of which composition as an auxiliary means is to ease the taking of oral medication in solid form, which composition comprises iota-carrageenan as a jellifying agent and citric acid as a salivating agent, characterized in that the composition further comprises 1.3%-1.8% maltodextrin. In another aspect, the composition comprises a calcium sequestrant for adjusting Ca-ion activity of the composition. In one embodiment, the composition comprises iota-carrageenan in 0.7-1.0% in mass, citric acid in 0.06% in mass, maltodextrin in 1.5% in mass, all relative to the total mass of the composition, and an amount of a calcium sequestrant such that the Ca-ion activity of the composition is between 20 ppm and 80 ppm.

The invention claimed is:

1. An oral composition in the form of a jelly to aid in the delivery of a solid-form oral medication, wherein the oral composition comprises:
   (i) iota-carrageenan,
   (ii) citric acid, and
   (iii) maltodextrin, wherein
   the oral composition comprises the iota-carrageenan and the citric acid as a nascent composition, and wherein the maltodextrin is added as a separate component to the nascent composition in an amount within a range of 0.5-2.0 mass %, based on the total mass of the oral composition, so that the oral composition exhibits a yield stress of 15 Pa or higher at 20° C. as measured using a Brookfield DX3TRVT rheometer that makes use of a controlled-stress ramp to gradually increase the amount of force on the sample until flow is initiated.

2. The oral composition according to claim 1, wherein hydroxypropyl methylcellulose, gelatin, spilanthol, jambu oleoresin, agar, carob, carboxy methylcellulose or xanthan gum are not present in the composition.

3. The composition according to claim 1, wherein the maltodextrin is present in the composition in an amount of 1.3-1.8 mass %, based on the total mass of the composition.

4. The composition according to claim 1, wherein the citric acid is present in the composition in an amount of 0.05 to 0.10 mass %, based on the total mass of the composition.

5. The composition according to claim 1, wherein the citric acid is present in the composition in an amount sufficient to achieve a pH of the composition within a range of 4.8 to 6.5.

6. The composition according to claim 1, wherein the composition further comprises a calcium sequestrant in an amount sufficient to adjust Ca-ion activity of the composition to achieve a Ca-ion activity of the composition which is <500 ppm.

7. The composition according to claim 6, wherein the calcium sequestrant is calcium chloride.

8. The composition according to claim 6, wherein the calcium sequestrant is calcium carbonate.

9. The composition according to claim 7, wherein the calcium chloride is present in the composition in an amount lower than 0.4 mass %, based on the total mass of the composition.

10. The composition according to claim 1, wherein the iota-carrageenan is present in the composition in an amount of 0.5 to 2 mass %, based on the total mass of the composition.

11. The composition according to claim 1, wherein the composition further comprises water in an amount of 80-99 mass %, based on the total mass of the composition.

12. The composition according to claim 1, wherein the composition further comprises a flavouring agent that provides the composition with a flavor selected from the group consisting of orange flavor, lemon flavor, lime flavor, red fruit flavor and mint flavor.

13. The composition according to claim 1, wherein the composition further comprises a sweetening agent selected from the group consisting of saccharose, aspartame, sucralose, *stevia* and inuline.

14. The composition according to claim 1, wherein the composition comprises 0.8 mass % of the iota-carrageenan, 0.06-0.07 mass % of the citric acid, 1.5 mass % of the maltodextrin and 0.005 mass % of calcium chloride, based on the total mass of the composition.

15. The composition according to claim 1, wherein the composition further comprises 0.005-0.4 mass % of calcium chloride, based on the total mass of the composition.

16. The composition according to claim 3, wherein the maltodextrin in the composition is present in the composition in an amount of 1.5 mass %, based on the total mass of the composition.

17. The composition according to claim 4, wherein the citric acid is present in the composition in an amount of 0.05 to 0.10 mass %, based on the total mass of the composition.

18. The composition according to claim 5, wherein the citric acid is present in the composition in an amount sufficient to achieve a pH of the composition of 5.5.

19. The composition according to claim 6, wherein the calcium sequestrant is present in an amount sufficient to achieve a Ca-ion activity of the composition which is between 10 ppm and 100 ppm.

20. The composition according to claim 6, wherein the calcium sequestrant is present in an amount sufficient to achieve a Ca-ion activity of the composition which is between 20 ppm and 80 ppm.

21. The composition according to claim 9, wherein the calcium chloride is present in the composition in an amount of 0.005-0.015 mass %, based on the total mass of the composition.

22. The composition according to claim 10, wherein the iota-carrageenan is present in the composition comprised in an amount of 0.7 to 1.0 mass %, based on the total mass of the composition.

23. The composition according to claim 10, wherein the water is present in the composition in an amount of 84-97 mass %, based on the total mass of the composition.

24. The composition according to claim 15, wherein the calcium chloride is present in an amount of 0.005-0.015 mass %, based on the total mass of the composition.

25. The composition according to claim 1, wherein the composition comprises:
   (i) 1.5 mass % of the maltodextrin,
   (ii) 0.80 mass % of the iota-carrageenan,
   (iii) 0.055 mass % of aspartame,
   (iv) 0.070 mass % of the citric acid,
   (v) 0.80 mass % of potassium sorbate, and
   (vi) 0.00-0.40 mass % of calcium chloride.

26. The composition according to claim 1, wherein the composition comprises:
   (i) 0.5-2.0 mass % of the maltodextrin,
   (ii) 0.80 mass % of the iota-carrageenan,
   (iii) 0.055 mass % of aspartame,
   (iv) 0.070 mass % of the citric acid,
   (v) 0.80 mass % of potassium sorbate, and
   (vi) 0.005 mass % of calcium chloride.

27. A solid-form oral medication which includes a coating comprised of the composition according to claim 1.

* * * * *